United States Patent [19]

Fasel et al.

[11] Patent Number: 5,736,358
[45] Date of Patent: Apr. 7, 1998

[54] DICTYOSTELID EXPRESSION VECTOR AND METHOD FOR EXPRESSING A DESIRED PROTEIN

[75] Inventors: Nicolas Joseph Fasel, Epalinges; Christophe Dominique Reymond, Prilly, both of Switzerland

[73] Assignee: RMF Dictagene S.A., Switzerland

[21] Appl. No.: 451,405

[22] Filed: May 26, 1995

Related U.S. Application Data

[63] Continuation of Ser. No. 965,273, filed as PCT/EP92/01112, May 18, 1992 published as WO92/20806, Nov. 26, 1992, abandoned.

[30] Foreign Application Priority Data

May 17, 1991 [NL] Netherlands ............... 9100869

[51] Int. Cl.$^6$ ............... C12P 21/06; C12N 15/80; C12N 1/15; C07H 21/04
[52] U.S. Cl. ............... 435/69.1; 435/69.3; 435/171; 435/172.3; 435/243; 435/254.11; 435/320.1; 536/23.1; 536/24.1; 935/48
[58] Field of Search ............... 435/69.1, 69.3, 435/171, 172.3, 243, 254.11, 320.1; 536/23.1, 24.1; 935/48

[56] References Cited

U.S. PATENT DOCUMENTS 4,870,008  9/1989  Brake ............... 435/70

FOREIGN PATENT DOCUMENTS

| 0278941 | 8/1988 | European Pat. Off. ........ C12N 15/00 |
| WO9106644 | 5/1991 | WIPO ............... C12N 15/11 |

OTHER PUBLICATIONS

T. Dingermann et al., "Optimization and in situ detection of Escherichia coli beta–galactosidase gene expression in Dictyostelium discoideum", Gene, vol. 85, 1989, pp. 353–362.

M. Maniak et al., "Evidence for a feedback regulated back–up promoter which controls permanent expression of a Dictyostelium gene", Nuceleic Acid Research, vol. 18, No. 18, 1990, pp. 5375–5380.

C.D. Reymond et al., "Regulated expression of ras gene constructs in Dictyostelium transformants", Proc. Natl. Acad. Sci. USA, vol. 82, Oct. 1985, Genetics, pp. 7005–7009.

Chi–Hung Siu et al., "Molecular mechanisms of cell–cell interaction in Dictyostelium discoideum", Biochem. Cell Biol., vol. 66, No. 10, 10 Oct. 1988, pp. 1089–1099.

F. Vauti et al., "Regulation of the discoidin I gamma gene in Dictyostelium discoideum: indentification of individual promoter elements mediating induction of transcription and repression by cyclic AMP", Molecular and Cellular Biol., vol. 10 No. 8, Aug. 1990, American Soc. for Microbiology, pp. 4080–4088.

N. Fasel et al., "Dictyostelium discoideum as an expression host for the circumsprorozoite protein of Plasmodium falciparum", Gene, vol. 111, 15 Feb. 1992, Elsevier Science Publishers B.V., pp. 157–163.

Glenn et al (1988) Australian J. Biotech. 1(4), 46–51.

Maniak et al (1990) Nucleic Acids Res 18, 5375.

May, T et al. (1989) Identification of a Cis–Acting Element Controlling Induction of Early Gene Expression in Dictyostelium discoideum. Molec. Cell. Biol. 9(1), 4653–4659.

Poole, S.J. and Firtel, R.A. (1984) Conserved Structural Features are Found Upstream From the Three Co–Ordinately Regulated Discoidin I Genes of Dictyostelium discoideum. J. Mol. Biol. 172, 203–220.

Dynan, W.S. (1989), Modularity in Promoters and Enhancers. Cell 58(1), 1–4.

Wasylyk, B. (1988) Enhancers and Transcription Factors in the Control of Gene Expression. Biochem. Biophys. Acta 951, 17–35.

Caspers, P., et al. (1989) The Circumsporo Zoite Protein Gene From NF54, A Plasmodium falciparum Isolate Used in Malaria Vaccine Trials. Mole. Biochem. Parasit. 35, 185–190.

Rossi, J. et al. (1983) Biological Expression of an Eschrichia coli Consensus Sequence Promoter and Some Mutant Derivatives PNAS USA 80, 3203–3207.

Sambrook, J (1989) Molecular Cloning: A Laboratory Manual Second Ed. CSH Laboratory Press. Sec. 1.42–1.71 and 6.22–6.35.

Howard, P.K. et al., (1988) Establishment of a Transient Expression System for Dictyostelium discoideum NAR 16(6), 2613–2623.

Scopes, R.K. (1987) Protein Purification: Principles and Practice, Second Ed. Springer–Verlag, NY, Chap. 6 pp. 215–218 and Chap. 5 pp. 126–141.

Primary Examiner—Douglas W. Robinson
Assistant Examiner—Thanda Wai
Attorney, Agent, or Firm—Webb Ziesenheim; Bruening Logsdon Orkin & Hanson, P.C.

[57] ABSTRACT

The invention relates to recombinant DNA molecules comprising a Dictyostelium discoideum homologous promoter region, a heterologous DNA sequence with a Dictyostelium discoideum homologous peptide sequence capable of functioning as a leader peptide sequence positioned upstream thereof and in proper reading frame therewith, and a Dictyostelium discoideum homologous termination region, the heterologous DNA sequence encoding the desired functional polypeptide or intermediate thereof, said DNA sequence being positioned downstream from the promoter region and said termination region being positioned downstream from the DNA sequence. The invention also provides recombinant dictyostelid hosts as well as methods for preparing recombinant DNA molecules of the invention and for expressing recombinant polypeptides encoded by said recombinant DNA molecules in dictyostelid hosts. The invention in particular relates to the expression of the CS protein of Plasmodium falciparum.

27 Claims, 4 Drawing Sheets

```
              XbaI
          ┌──────┐
5' ATG TCT AGA TTT TTA GTA TTG ATA ATA TTA TAT AAT ATT
   TAC AGA TCT AAA AAT CAT AAC TAT TAT AAT ATA TTA TAA

TTA AAT AGT GCA CAT TCA GCT CCA ACC CAG GAT CCA TG    3'
   AAT TTA TCA CGT GTA AGT CGA GGT TGG GTC CTA GGT AC
                                       └──────┘
                                        BamHI
```

Fig. 1

```
                Rsa I                                Cla I
                ┌──┐                                 ┌──┐
  1  GTACATAATATTTTTGTGTTCTTATAATTTGGTTAAATCGATGAATAATA

51  TTTGATTAGTATATGTTTTTTTTCCTTTTTTTTATTTTTATTTTTATTT

101  TTTTAAAAAATAAAAATTAGAATAAAATATTTCTATTTGAAGGAGTTTTT

151  ATTTGTATTTAAAATTATATTAAACATAGTGAACCTAAAAATAGATTTGT
                                      ‾‾‾‾‾‾‾‾‾‾‾‾‾‾‾‾
201  GACGGTATATGATAAGAAAATTCTAAAAAAAAAATTCAGATAATTTTTGG
     ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
251  ATTGGAAACAACAACCAAAAAAAAAAAAAAAAAAAAAAAAAAAATCAAA
     ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾

301  AAAAAAAAAAAAAAAATTAAAATCAAAAAAAAAAGGTATTTAAAGAAATT
     ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                  ↓↓↓↓↓↓↓
351  TTTTAAAATATTATTATATATCTTTAATTGTGCAAAACACACTTTTAACA
     ‾‾‾‾‾‾‾‾‾‾‾‾‾‾‾‾‾‾‾‾‾

401  CACTCTATTATCTTACAAAGGTTTAAAATTTTAATTTTTTTATTTAATT
     *              *                *
     *              *
451  ATTATTTTTTAAATAAATTTTTTTAATTTTTAATTTTTTTTTTTTT
                                       ▼▼

501  TTACCATCAACCCCTTTAATCAAACAAATAACATTTATTATTTATTTATT
                                        ▼ ▼

551  TTATATATATCAATTAGAAATAAAAATATTTTCCTAATAGTAGTAATAAT
                                Rsa I
                                ┌──┐
601  AATTTCTTTTAATAAAAATACCTTTTGTACATTATTATTTTTTATTA

651  TTTTTTTCTTTAATCATTCAAAATTTTATTTTTTTTTTAAAAAAAAAA
                                              Met
701  AACAATTAAAACAAACAATTTAAAAAAAATG
```

Fig. 4

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 77
        ( B ) TYPE: NUCLEIC ACID
        ( C ) STRANDEDNESS: DOUBLE
        ( D ) TOPOLOGY: UNKNOWN ( x i ) SEQUENCE DESCRIPTION: SEQ ID NO: 1:

```
ATG TCT AGA TTT TTA GTA TTG ATA ATA TTA TAT AAT ATT          39
TTA AAT AGT GCA CAT TCA GCT CCA ACC CAG GAT CCA TG           77
```

( 2 ) INFORMATION FOR SEQ ID NO: 2:

( i ) SEQUENCE CHARACTERISTICS:
        ( A ) LENGTH: 731
        ( B ) TYPE: NUCLEIC ACID
        ( C ) STRANDEDNESS: SINGLE
        ( D ) TOPOLOGY: UNKNOWN ( x i ) SEQUENCE DESCRIPTION: SEQ ID NO: 2:

```
GTACATAATA TTTTGTGTT  CTTATAATTT GGTTAAATCG ATGAATAATA     50
TTTGATTAGT ATATGTTTTT TTTTCCTTTT TTTTATTTTT ATTTTTATTT    100
TTTTAAAAAA TAAAAATTAG AATAAAATAT TTCTATTTGA AGGAGTTTTT    150
ATTTGTATTT AAAATTATAT TAAACATAGT GAACCTAAAA ATAGATTTGT    200
GACGGTATAT GATAAGAAAA TTCTAAAAAA AAAATTCAGA TAATTTTTGG    250
ATTGGAAACA ACAACCAAAA AAAAAAAAAA AAAAAAAAAA AAAATCAAA     300
AAAAAAAAAA AAAAAATTAA AATCAAAAAA AAAAGGTATT TAAAGAAATT    350
TTTTAAAATA TTATTATATA TCTTTAATTG TGCAAAACAC ACTTTTAACA    400
CACTCTATTA TCTTACAAAG GTTAAAATT  TTAATTTTTT TTATTTAATT    450
ATTATTTTTT TAAATAAATT TTTTTTAATT TTTTAATTTT TTTTTTTTTT    500
TTACCATCAA CCCCTTTAAT CAAACAAATA ACATTTATTA TTTATTTATT    550
TTATATATAT CAATTAGAAA TAAAAATATT TTCCTAATAG TAGTAATAAT    600
AATTTCTTTT TAATAAAAAT ACCTTTTTCT ACATTATTAT TTTTTATTA     650
TTTTTTTCTT TAATCATTCA AAATTTTATT TTTTTTTTTA AAAAAAAAA     700
AACAATTAAA ACAAACAATT TAAAAAAAAT G                        731
```

( 2 ) INFORMATION FOR SEQ ID NO: 3:

( i ) SEQUENCE CHARACTERISTICS:
        ( A ) LENGTH: 25
        ( B ) TYPE: AMINO ACID
        ( C ) STRANDEDNESS: SINGLE
        ( D ) TOPOLOGY: UNKNOWN ( x i ) SEQUENCE DESCRIPTION: SEQ ID NO: 3:

Met Ser Arg Phe Leu Val Leu Ile Ile Leu Tyr Asn Ile Leu Asn
1               5                   10                  15

Ser Ala His Ser Ala Pro Thr Gln Asp Pro
                20                  25

DICTYOSTELID EXPRESSION VECTOR AND METHOD FOR EXPRESSING A DESIRED PROTEIN

This is a continuation of application Ser. No. 07/965,273 filed as PCT/EP92/01112, May 18, 1992 published as WO92/20806, Nov. 26, 1992, abandoned.

FIELD OF THE INVENTION

The present invention relates to recombinant DNA molecules and a method for expressing desired DNA sequences in dictyostelids. More in particular it relates to a recombinant plasmid and method for expressing a desired enzyme or parasite antigen in dictyostelids and more in particular to expressing the circumsporozoite antigen of *Plasmodium falciparum* and chloramphenicol acetyl transferase in *Dictyostelium discoideum*.

BACKGROUND OF THE INVENTION

Production of functional or immunogenic recombinant polypeptides has been obtained in multiple organisms. In general, the gene of interest has been isolated and expressed under the control of specific DNA elements allowing expression in the particular host. Bacteria, lower and higher eukaryotic cells and viral vectors have been among the most widely used systems.

*Plasmodium falciparum*, the most frequent human malaria cadsatire parasite, is found in different forms in insect and human hosts. The use of inactivated parasite forms as vaccine in mammals have shown promising results. A limitation, however, being the low amount of material available due to the difficulty of cultivating parasites. The genes coding for some cell surface proteins of the different forms have been sequenced allowing identification of host protective antigens possibly useful as vaccines. Expression of such antigens or other *P. falciparum* proteins in heterologous recombinant systems (e.g. *E. coli*, yeast, vaccinia virus, baculovirus, salmonella) has been difficult, and in most instances, only small amounts of complete proteins were obtained.

The surface of the first form of *Plasmodium falciparum* found in the organism after insect bite transmission, is covered by the circumsporozoite (CS) protein. This protein is synthesized in the form of a polypeptide precursor which is composed of an amino terminal signal sequence removed upon processing, of a large central repeat domain flanked on both sides by regions referred as region I and II containing conserved sequences between different Plasmodia species and of a terminal carboxy anchor domain. The repeat domain consisting of (ASN-ALA-ASN-PRO)$_n$ has been shown to be the B-cell immunodominant region of the *P. fatciparum* CS. Synthetic peptides containing such a repeat have been used with limited success as subunit vaccine in protection studies. The T-cell response elements on the CS protein have been mapped outside of the repeat segments. These results suggest that the entire CS protein could be used to obtain a stronger and longer lasting immune protection. These experimental data further indicate the requirement for a protein with its B- and T-cell epitopes to obtain an efficient malaria vaccine.

Difficulties in producing high amounts of CS protein were bypassed by expressing only segments of the CS protein in vivo which, however, did not elicit a sufficient immune response as vaccines. Expression of the complete protein was obtained using vaccinia and baculovirus expression systems. However, unstable expression of proteins as well as the high cost of production render such systems unattractive.

It is therefore an object of the present invention to provide an expression system for different kinds of proteins, such as *Plasmodium falciparum* proteins, that is capable of stable expression of proteins at low cost.

DETAILED DESCRIPTION OF THE INVENTION

It has been found that species of the slime mold Dictyostelium can be used as an efficient eukaryotic expression system for the production of recombinant proteins.

The cellular slime mold *Dictyostelium discoideum* (Dd) is a free-living organism, easy to grow and to maintain. Dd strains can grow on bacteria lawns with a doubling time of about 3 hours, in bacterial suspensions to high densities (up to $10^{10}$ cells per liter) or in semi-synthetic media containing glucose, peptone and yeast extract where doubling time is about 12 hours. The life cycle of Dictyostelium consists of a growth and a developmental phase. The developmental phase is triggered by starvation and is characterized by aggregation of previously single cells to form a multicellular organism which then differentiates to produce spores which can be stored over a prolonged period of time. Germination of spores in the presence of bacteria or rich medium will allow renewed growth. During this developmental cycle, diffusible factors are produced and for at least one of them (cAMP) binding to its receptor induces transcription of a set of specific genes (See Loomis, The development of *Dictyostelium discoideum*, Acad. Press, 1982).

Growth properties and transformation capacity of *Dictyostelium discoideum* offers the possibility to express foreign proteins, since cells can be grown at low cost on bacteria and expression of specific proteins can be tightly controlled by starvation in a simple medium.

In one embodiment of this invention the homologous promoter region is the Discoidin I promoter of *Dictyostelium discoideum* which is under developmental control. Transcription from this promoter is induced by starvation of the Dictyostelium cell culture.

Furthermore a leader peptide sequence [SEQ ID NO: 1] is provided in the expression vector. The DNA sequence of SEQ ID NO: 1 inherently encodes for the following amino acid sequence (SEQ ID NO: 3):

Met Ser Arg Phe Leu Val Leu Ile Ile Leu Tyr Asn Ile

Leu Asn Ser Ala His Ser Ala Pro Thr Gln Asp Pro

Fusion of this leader peptide allows export of the recombinant protein to the cell surface thus facilitating recombinant protein identification.

In another embodiment the invention provides an inducible expression vector. The Dd ras promoter [SEE SEQ ID NO: 2] of *Dictyostelium discoideum* is used there as the homologous promoter region. Expression of genes under the control of the Dd ras promoter is triggered by cAMP addition to the cell culture. During cell growth the transcription level from the Dd ras promoter is undetectable, thus allowing to introduce genes encoding potentially toxic proteins in Dictyostelium. The production of these proteins is triggered by cAMP addition during development.

BRIEF DESCRIPTION OF THE DRAWINGS

FIG. 1 displays the nucleic acid sequence (SEQ ID NO:) of the *Dictyostelium discoideum* homologous leader peptide discussed herein;

FIG. 4 shows the DNA sequence (SEQ ID NO: 2) of the RsaI fragment discussed herein.

Figure 2:
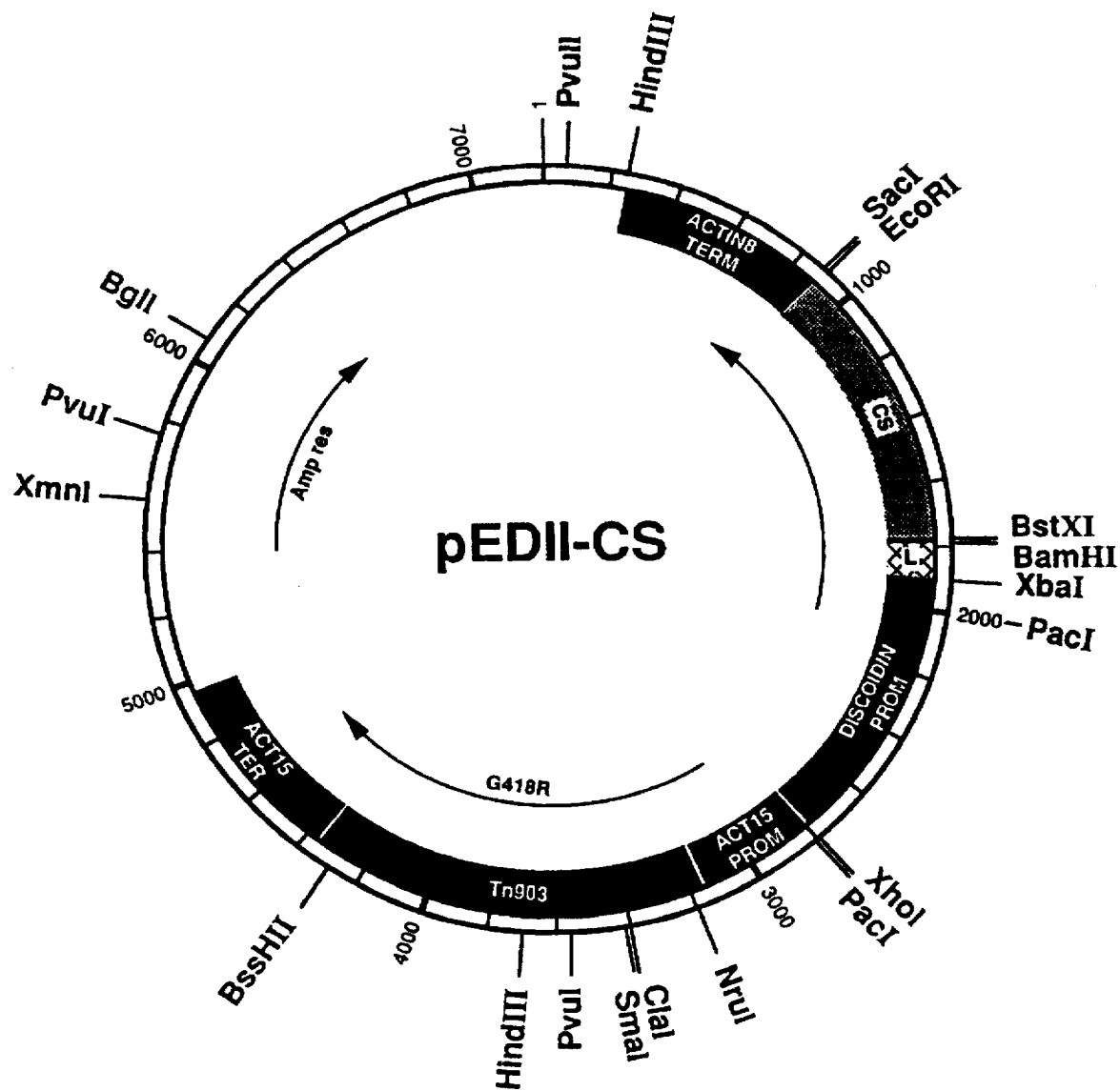
FIG. 2 is an illustration of expression vector pEDII-CS.

The invention is further illustrated by the following examples, which should not be considered as limiting the scope of the present invention.

A deposit of *Dictyostelium discoideum* designated by accession No. CBS 238.91 was made with Centraalbureau voor Schimmelcultures, Oosterstraat 1, P.O. Box 273, 3740 AG BAARN, The Netherlands, on Aug. 22, 1991, depositor's reference designation pEDII-CS.

EXAMPLES

The following examples utilize many techniques well known and accessible to those skilled in the art of molecular biology. Such methods are not always described in detail.

Enzymes are obtained from commercial sources and used according to the supplier's protocols.

Bacterial media and current cloning techniques are described in Sambrook et al. (Molecular cloning: A laboratory manual, CSH Press, 1989.)

Monoclonal antibodies and NANP$_{50}$ peptide were obtained from H. Matile (Hoffman La Roche Ltd.).

Example 1

The following examples teach the expression of the circumsporozoite antigen CS of *Plasmodium falciparum* in *Dictyostelium discoideum* under the control of the Discoidin I promoter.

1.1. Construction of CS containing plasmids.

Expression vector pEDI-CS is constituted of the pVEII vector (Maniak and Nellen, Nucl. Acids Res., 18, 5375, 1990), which contains the elements important for propagation and maintenance in a prokaryotic host (origin of replication and ampicillin resistance), and of a Tn903 encoded neomycin resistance gene conferring geneticin (G418) resistance to eukaryotic cells under the control of a Dictyostelium actin 15 transcription unit. The presence of a Discoidin I promoter allows the developmental control of expression of downstream sequences and actin 8 sequences insure proper termination of the RNA.

For construction of the pEDI-CS expression vector the HaeIII+RsaI restriction fragment of 1161 bp of the CS NF54 gene (Caspers et al., Mol. and Biochem. Parasitol 35, 185, 1989) was first inserted onto the Asp718+BamHI site of pVEII filled in by Klenow DNA polymerase.

Subsequently both DNA strands of a sequence encoding the contact site A (CsA) leader peptide plus 3 amino acids were synthesized on a Applied Biosystem Model 380 B DNA synthesizer. The nucleotide sequence of the synthetic leader peptide [SEQ ID NO: 1] (FIG. 1) was confirmed by introducing the blunt end fragment onto M13mp18 replicative form at the SmaI site, followed by DNA sequencing.

The XbaI+BamHI restriction fragment containing CsA leader peptide was then isolated and inserted at the XbaI+Bam HI sites present in the vector to generate expression vector pEDII-CS.

1.2. Transformation of *Dictyostelium discoideum*.

Dictyostelium cells were cultured in shaking suspensions in HL-5 medium up to a concentration of 2-5×10$^6$/ml, centrifuged at 300 g and rinsed in distilled water. 5 µg of the desired DNA was electroporated onto 10$^7$ cells in 100 µl of distilled water at 670 V and 3 µF using a Gene Pulser apparatus from BioRad, thus delivering a pulse of about 1.5 msec.

Progressive G418 selection was applied to the cells up to a concentration of 50 µg/ml, ensuring the presence of 100 to 200 copies of tandem repeats of inserted DNA.

1.3. CS expression upon starvation at the RNA level.

RNA was prepared from cells grown in HL-5 medium (vegetative stage) or after 4, 8 or 15 hours of starvation in PDF, respectively.

Therefor 10$^7$ cells were lysed in 50 mM Tris pH 8.5, 0.1% SDS, 1 mM vanadyl complex and extracted 3 times with phenol-chloroform 1:1.

15 µg of RNA were treated with glyoxal and subjected to electrophoresis on a 0.8% agarose gel. The samples were transferred to Genescreen plus filters with a vacugene apparatus. Anti-sense RNA probes were generated by inserting DNA fragments onto the vector pGEM-1, and carrying out Sp6-RNA polymerase reactions. The filters were hybridized for 48 hours at 55° C. in a solution containing 50% formamide, 5XSSC (1XSSC=0.15M NaCl, 15mM sodium citrate), 0.2% bovine serum albumin, 0.2% Ficoll, 0.2% polyvinylpyrrolidone, 25mM Na$_2$- HPO$_4$, 25mM NaH$_2$PO$_4$, 0.2% SDS, 1mM EDTA, 250 µg/ml denatured DNA and 500 µg/ml yeast RNA. The filters were washed 5=15 min. in 0.1XSSC, 0.12% SDS at 65° C.

On the Northern blots, an RNA species of 1.4 kb was detected in pEDII-CS transfected cell, whereas no signal was detected in pVEII transfected cells. The amount of steady-state CS RNA increases after 4 hours of starvation, followed by a decrease in expression after 15 hours.

1.4. CS expression upon starvation at the protein level.

Proteins were prepared from the same aliquots used in example 1.3. for the analysis of CS expression upon starvation at the protein level.

Cells were lysed in 1 X Laemmli's buffer at 100° C. for 5 min. and proteins were separated on a 10% SDS-PAGE. Proteins were electrotransferred onto a nitrocellulose filter. 0.2 mg/ml of the anti-NANP monoclonal antibody was added to the filter for an overnight incubation at room temperature. $^{125}$I-protein A was used to reveal the anti-NANP reaction.

The Western blots showed no CS expression in pVEII cells and a maximal expression in pEDII-CS cells after 4 hours of starvation. A single band of 62 kDA molecular mass was detected. No other crossreacting species was observed. This induction of the expression follows the profile expected for Discoidin I gene regulation.

1.5. Recognition of the NANP epitope on the CS protein.

To confirm recognition of the NANP epitope present on the CS protein, the binding of an anti-NANP monoclonal antibody to the Dd expressed CS protein was competed with a NANP$_{50}$ peptide. Cells expressing the CS polypeptide were lysed, proteins separated by SDS-PAGE and transferred onto a nitrocellulose filter. Before incubation, the anti-NANP$_{50}$ monoclonal antibody was incubated with different amount of a NANP$_{50}$ peptide which correspond to the number of NANP$_{50}$ repeats present on the CS protein. A tenth equimolar amount of NANP$_{50}$ peptide was sufficient to observe a significant reduction in the binding of the monoclonal antibody to the CS protein.

1.6. Recognition of different *Plasmodium falciparum* CS epitopes by monoclonal antibodies.

Different monoclonal antibodies against CS proteins or synthetic peptides were used in the immunoblot assay. Dd cells were lysed, proteins separated by SDS-PAGE and transferred onto a nitrocellulose filter. Filter strips were incubated with different monoclonal antibodies from various categories (SP3B4, SP3.E9, CT3.3, CT3.1, SP3.H3, SP3.E6, SP3.C6). Recognition of epitopes was visible only with the expected antibodies. In no cases, a specific signal was observed in cells expressing pVEII vector only.

1.7. Purification of CS protein produced in *Dictyostelium discoideum*.

At the amino acids level, the CS protein contains a carboxy terminal hydrophobic segment which could play a role as a signal for the addition of a glycosyl-phosphatidylinositol anchor (GPI). This C-terminal peptide segment or a posttranslationally added GPI anchor should confer a hydrophobic nature to the CS protein thus allowing its partitioning in Triton X-114.

Proteins were extracted from the cells with 1% of Triton X-114 and separated into aqueous and detergent phases. The detergent soluble proteins were analyzed by Western blot. At least 10 times more proteins were present in the aqueous phase than in the TX-114 phase estimated by a Biorad Protein assay and also as judged by Ponceau staining. A strong signal is observed in the TX-114 phase of CS expression cells, even though a certain amount of protein still remains in the aqueous phase. No signal is found in the pVEII sample. Treatment with Triton X-114 therefore allows a first partial purification of the recombinant protein.

Figure 3:
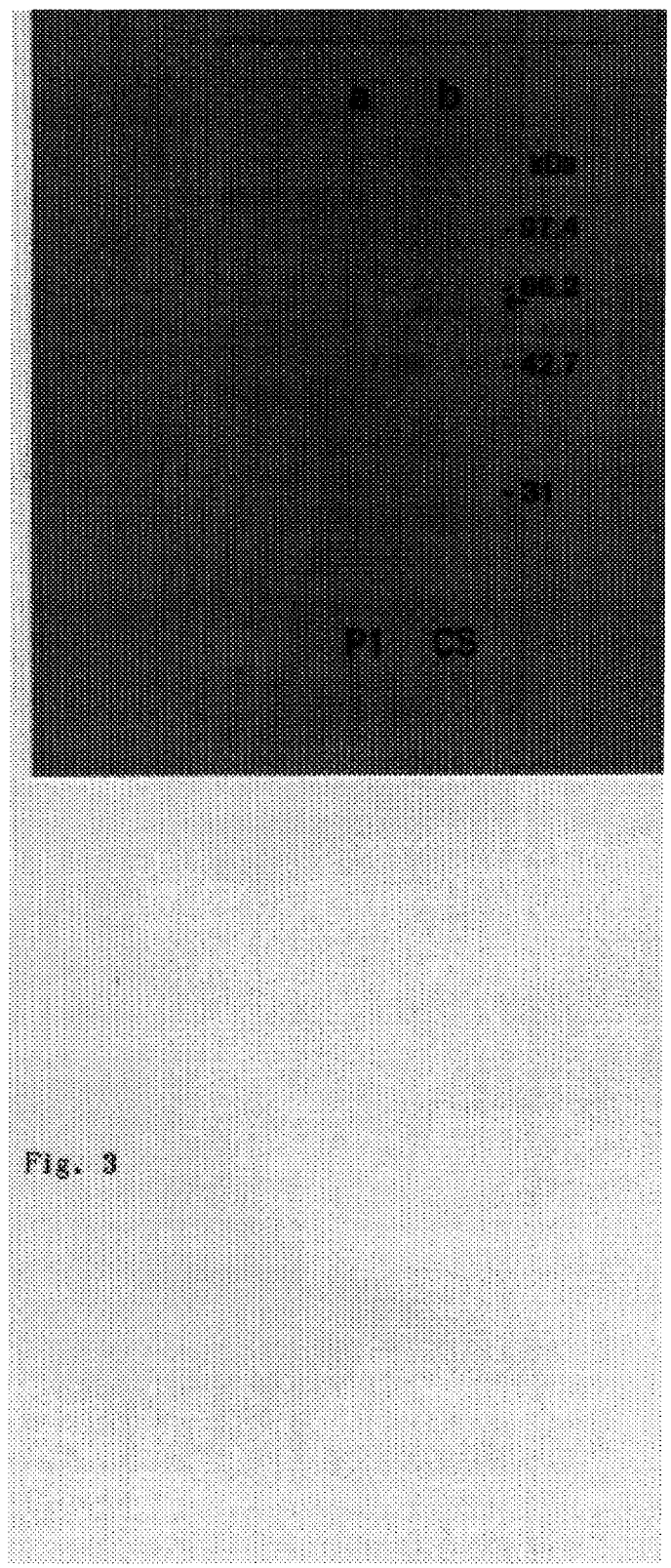
FIG. 3 shows the comparative banding results of analysis of pVEII- and pEDII-CS- containing cells.

In order to further purify CS protein expressed in Dictyostelium, CS cells were pulse-labelled with [$^{35}$S]-methionine for 2 hours after an initial starvation period of two hours. Cells were removed by centrifugation, lysed in Crumpton lysis buffer and precleaned with protein A Sepharose. TX-114 soluble proteins were loaded on an affinity column containing anti-NANP antibody crosslinked to Sepharose. After elution from the column in the presence of 0.1 M glycine (pH 2.5) methionine-labelled protein with an apparent molecular weight of 62kDa was detected by SDS-PAGE and fluorography. The same experiment performed on pVEII containing cells revealed only minor bands of different molecular weights (FIG. 3).

1.8. Cell surface expression.

If correctly processed, the CS protein should be present on the cell surface. Analysis of fluorescent activated cell sorting using an anti-NANP antibody showed that the CS protein is expressed at the surface of *Dictyostelium discoideum* cells.

1.9. Terminal sequencing.

In order to determine whether the expressed CS protein was complete, CS protein was isolated, using Triton TX-114 phase separation and immunoaffinity chromatography, to sequence its N-terminus.

No sequence could be obtained from the complete protein, indicating a probable block at the amino terminus. When the purification was done in presence of fewer protease inhibitors, an amino acid sequence missing the first 25 amino acids was obtained. When only benzamidine was used up to 33 amino acids were absent from the N-terminus suggesting that endogenous protease could attack the CS protein during its purification. As shown, this problem can be solved by using protease inhibitors and is limited to the first 20 amino acids.

Example 2

The following example teaches the expression of the circumsporozoite antigen CS of *Plasmodium falciparum* in *Dictyostelium discoideum* fused to a leader peptide from contact site A and under the control of an inducible promoter (Dd ras)

2.1. DNA-sequence of the Dd ras promoter

The DNA-sequence of the Dd ras promoter used in this example is identical to nucleotides 1 to 401 [SEE SEQ ID NO: 2] from FIG. 4 (see also example 3)

2.2. Construction of pERI-CS vector

The Discoidin I promoter region of pEDII-CS was excised using PacI resriction digestion, leaving 68 nucleotides of transcribed but untranslated Discoidin I sequence, the AUG codon, the contact site A leader peptide and the CS coding region (see FIG. 2). A Dd ras promoter fragment encompassing nucleotides 1 to 401 of FIG. 4 was obtained by exonuclease III digestion and addition of BamHI linkers. After blunt ending with T4-polymerase, this fragment was ligated in the above mentioned PacI digested CS vector to obtain pERI-CS 2.3. Expression of the CS protein The construct pERI-CS of example 2.2. was reintroduced into Dictyostelium and cells analyzed for CS expression by Western blot (see example 1.4.; results not shown). CS expression was very low in vegetative cells starved in suspension in PDF. An increase of about 100 fold was observed in the level of CS protein already after one hour of cAMP addition (0.2 mM). Two hours of induction further increased expression whereas the level of CS protein decreased after 16 hours of incubation.

Example 3

The following example teaches the expression of chloramphenicol acetyl transferase in *Dictyostelium discoideum* using an inducible expression vector.

3.1. DNA sequence of the Dd ras promoter.

The RsaI restriction fragment from the genomic clone of Dd ras was inserted into the SmaI site from pGEM1. Sequencing was performed using specific primers on double stranded DNA.

FIG. 4. shows the DNA sequence of the RsaI fragment. Arrows indicate transcription start sites. The thick arrow corresponds to the major transcript detected upon external cAMP addition. Dotted arrows indicate further RNA start site used during normal Dd development. Met is the Dd ras protein start codon. The region essential for promoter function is underlined. * corresponds to the breakpoint of a 3' deletion providing a DNA fragment comprising nucleotides 1 to 434;  indicates the breakpoint of a 3' deletion providing a DNA fragment comprising nucleotides 1 to 401; * corresponds to the breakpoint of a 5' deletion providing a DNA fragment comprising nucleotides 418–630.

3.2. Construction of the CAT containing vector.

Parts of Dd ras promoter sequences were placed in pAV-CAT vector (May et al., Mol. Cell Biol. 9, 4653, 1989). The resulting constructs resemble pEDII-CS with CS and leader peptides replaced by a chloramphenicol acetyl transferase gene (CAT), Discoidin I promoter by Dd ras promoter and the G418 resistance gene under the control of the actin 15 promoter and terminator region placed in opposite orientation.

3.3. Expression of chloramphenicol acetyl transferase in *Dictyostelium discoideum* on the RNA level.

The constructs of example 2.2. were reintroduced in Dictyostelium and cells analyzed for CAT expression on the RNA level.

RNA was prepared from Dd cells transformed with a recombinant pAV-CAT vector containing parts of the RsaI fragment of the Dd ras promoter. RNA was isolated from cells starved for 7 hours. Half of the cells received cAMP (0.2mM) for 1 hour before RNA preparation. After separation on agarose gel (MES-glyoxal) and transfer to Genescreen, the RNA was probed with pAV-CAT whole vector labelled by nick translation.

CAT transcripts were detectable after cAMP induction with Dd ras promoter fragments containing at least the sequence underlined in FIG. 4. Further deletions abolished CAT RNA accumulation. Optimal CAT transcript accumulation occurred with a DNA containing sequence 1 to 401 (** in FIG. 4).

3.4. Expression of chloramphenicol acetyl transferase in *Dictyostelium discoideum* at the enzyme level.

10⁷ Dd cells containing pAV-CAT vectors with nucleotides 1 to 434, 1 to 401 and 418 to 630 [SEE SEQ ID NO: 2] respectively were lysed by 3 cycles of freezing and thawing. After centrifugation at 12'000 rpm for 5 min. CAT activity in supernatant was assayed for 30 min. by described techniques (Gorman et al., Mol. Cell. Biol. 2, 1044, 1982).

Due to large amounts of CAT activity in the extracts, only 1 µl out of 50 µl of supernatant was used to insure being in the linear phase of the reaction.

CAT activity assays showed not only the presence of a functional enzyme in Dd extracts, but also induction with the proper constructs.

We claim:

1. A recombinant DNA molecule suitable for the expression of a desired polypeptide in a dictyostelid host, wherein the recombinant DNA molecule comprises a *Dictyostelium discoideum* homologous promoter region, a Dictyostelium homologous sequence encoding an amino acid sequence functioning as a leader peptide positioned upstream of a heterologous sequence encoding the desired polypeptide in proper reading frame therewith, and a *Dictyostelium discoideum* homologous termination region, said leader peptide having an amino acid sequence of SEQ ID NO: 3 and being encoded by the *Dictyostelium discoideum* Contact Site A gene, said heterologous DNA sequence being positioned downstream from the promoter region and said termination region being positioned downstream from the heterologous DNA sequence.

2. A recombinant DNA molecule according to claim 1 wherein the dictyostelid host is *Dictyostelium discoideum*.

3. A recombinant DNA molecule according to claim 1 wherein the promoter region is the Discoidin I promoter of *Dictyostelium discoideum*.

4. A recombinant DNA molecule according to claim 1 wherein the promoter region is the Dd ras promoter of *Dictyostelium discoideum*.

5. A recombinant DNA molecule according to claim 1 wherein the promoter region is composed of basepairs 1 to 401 of SEQ ID NO: 2.

6. A recombinant DNA molecule according to claim 1 wherein the heterologous DNA sequence encodes a parasite protein.

7. A recombinant DNA molecule according to claim 6 wherein the parasite protein is a human or animal parasite protein.

8. A recombinant DNA molecule according to claim 7 wherein the protein is a Plasmodium protein.

9. A recombinant DNA molecule according to claim 8 wherein the Plasmodium protein is a *Plasmodium falciparum* protein.

10. A recombinant DNA molecule according to claim 9 wherein the *Plasmodium falciparum* protein is the circumsporozoite antigen.

11. A recombinant DNA molecule according to claim 1 wherein the DNA sequence of the *Dictyostelium discoideum* homologous leader peptide is the sequence of SEQ ID NO: 1.

12. A recombinant DNA molecule according to claim 1 wherein the heterologous DNA sequence encodes a protein with enzymatic activity.

13. A dictyostelid strain comprising a recombinant DNA molecule according to claim 1.

14. A dictyostelid strain comprising a recombinant DNA molecule according to claim 1 and expressing the circumsporozoite antigen from *Plasmodium falciparum*.

15. A dictyostelid strain expressing an enzymatically active protein obtained by a recombinant DNA molecule according to claim 12.

16. *Dictyostelium discoideum* (pEDII-CS) having the deposit accession number CBS 238.91.

17. Method for producing a recombinant DNA molecule for expression of a desired polypeptide in dictyostelids comprising:
  a) linearizing a DNA molecule containing Dictyostelium homologous promoter and terminator sequences to obtain a linear DNA molecule;
  b) isolating a heterologous DNA sequence encoding the desired polypeptide;
  c) ligating said linearized DNA molecule and said isolated DNA sequence to obtain a first recombinant DNA molecule;
  d) synthesizing a leader peptide sequence according to SEQ ID NO: 1;
  e) linearizing the first recombinant plasmid of step c) to obtain linearized plasmid DNA; and
  f) ligating said linear recombinant plasmid and said synthesized leader peptide sequence to obtain a second recombinant DNA molecule for transformation of a dictyostelid host.

18. Method according to claim 17 for producing recombinant plasmids pEDII-CS, wherein the DNA molecule containing *Dictyostelium discoideum* homologous promoter and terminator sequences is pVEII, the heterologous DNA sequence is the CS NF54 gene of *Plasmodium falciparum*, the first recombinant plasmid is pEDII-CS, and the leader peptide sequence is the sequence according to SEQ ID NO: 1.

19. Method for producing recombinant polypeptides, which method comprises:
  a) preparing an expression vector according to claim 1 encoding a desired polypeptide sequence;
  b) transforming a dictyostelid host cell culture with said expression vector to obtain a recombinant dictyostelid host cell;
  c) culturing said recombinant dictyostelid host cell under conditions permitting expression of the DNA sequence encoding the desired recombinant polypeptide; and
  d) recovering said recombinant polypeptide.

20. Method according to claim 19 wherein the desired polypeptide is a parasite protein.

21. Method according to claim 20 wherein the desired polypeptide is a human or animal parasite protein.

22. Method according to claim 21 wherein the desired parasite polypeptide is a Plasmodium spp protein.

23. Method according to claim 22 wherein the Plasmodium spp protein is a *Plasmodium falciparum* protein.

24. Method according to claim 23 wherein the *Plasmodium falciparum* protein is the circumsporozoite antigen.

25. Method according to claim 19 wherein the desired polypeptide is a polypeptide having enzymatic activity.

26. Method according to claim 19 wherein the dictyostelid host cell culture is *Dictyostelium discoideum*.

27. Method according to claim 19 wherein the conditions permitting expression of the DNA sequence comprise starving the Dictyostelium cell culture.

* * * * *